United States Patent [19]
Wang et al.

[11] Patent Number: 5,631,142
[45] Date of Patent: May 20, 1997

[54] COMPOSITIONS COMPRISING BONE MORPHOGENETIC PROTEIN-2 (BMP-2)

[75] Inventors: Elizabeth A. Wang, Carlisle; John M. Wozney, Hudson; Vicki A. Rosen, Brookline, all of Mass.

[73] Assignee: Genetics Institute, Inc., Cambridge, Mass.

[21] Appl. No.: 118,363

[22] Filed: Sep. 7, 1993

Related U.S. Application Data

[60] Continuation of Ser. No. 884,353, May 18, 1992, abandoned, which is a division of Ser. No. 378,537, Jul. 11, 1989, Pat. No. 5,166,058, which is a continuation-in-part of Ser. No. 179,100, Apr. 8, 1988, Pat. No. 5,013,649, which is a continuation-in-part of Ser. No. 28,285, Mar. 20, 1987, abandoned, which is a continuation-in-part of Ser. No. 943,332, Dec. 17, 1986, abandoned, which is a continuation-in-part of Ser. No. 880,776, Jul. 1, 1986, abandoned.

[51] Int. Cl.$^6$ .............................. C07K 14/51; C12N 15/12
[52] U.S. Cl. ........................ 435/69.1; 530/300; 530/350; 530/399; 514/2
[58] Field of Search ................................. 530/300, 350, 530/399; 514/2; 435/69.1

Primary Examiner—Vasu Jagannathan
Assistant Examiner—Elizabeth C. Kemmerer
Attorney, Agent, or Firm—Ellen J. Kapinos; Thomas J. DesRosier

[57] ABSTRACT

Purified BMP-2 proteins and processes for producing them are disclosed. The proteins may be used in the treatment of bone and cartilage defects and in wound healing and related tissue repair.

12 Claims, 7 Drawing Sheets

FIGURE 1

```
(1)                  15                        30                         45
GGC CAC GAT GGG AAA GGA CAC CCT CTC CAC AGA AGA GAA AAG CGG
 G   H   D   G   K   G   H   P   L   H   R   R   E   K   R 60                        75                     90
CAA GCA AAA CAC AAA CAG CGG AAA CGC CTC AAG TCC AGC TGT AAG
 Q   A   K   H   K   Q   R   K   R   L   K   S   S   C   K

(32)            105                       120                    135
AGA CAC CCT TTA TAT GTG GAC TTC AGT GAT GTG GGG TGG AAT GAC
 R   H   P   L   Y   V   D   F   S   D   V   G   W   N   D 150                       165                    180
TGG ATC GTT GCA CCG CCG GGG TAT CAT GCC TTT TAC TGC CAT GGG
 W   I   V   A   P   P   G   Y   H   A   F   Y   C   H   G 195                       210                    225
GAG TGC CCT TTT CCC CTG GCC GAT CAC CTT AAC TCC ACG AAT CAT
 E   C   P   F   P   L   A   D   H   L   N   S   T   N   H 240                       255                    270
GCC ATT CTC CAA ACT CTG GTC AAC TCA GTT AAC TCT AAG ATT CCC
 A   I   V   Q   T   L   V   N   S   V   N   S   K   I   P 385                       300                    315
AAG GCA TGC TGT GTC CCA ACA GAG CTC AGC GCC ATC TCC ATG CTG
 K   A   C   C   V   P   T   E   L   S   A   I   S   M   L 330                       345                    360
TAC CTT GAT GAG AAT GAG AAG GTG GTA TTA AAG AAC TAT CAG GAC
 Y   L   D   E   N   E   K   V   V   L   K   N   Y   Q   D
                                                  _____

375            (129)       397           407
ATG GTT GTC GAG GGT TGT GGG TGT CGT TAGCACAGCA AAATAAAATA
 M   V   V   E   G   C   G   C   R
_____

417         427        437         447         457
TAAATATATA TATATATATA TTAGAAAAAC AGCAAAAAAA TCAAGTTGAC 467         477        487         497         507
ACTTTAATAT TTCCCAATGA AGACTTTATT TATGGAATGG AATGGAGAAA 517         527        537         547         557
AAGAAAAACA CAGCTATTTT GAAAACTATA TTTATATCTA CCGAAAAGAA 567         577        587
GTTGGGAAAA CAAATATTTT AATCAGAGAA TTATT
```

FIGURE 2

```
        10         20         30         40         50         60         70
GTCGACTCTA GAGTGTGTGT CAGCACTTGG CTGGGACTT CTTGAACTTG CAGGGAGAAT AACTTGCGCA 80         90        100        110        120        130        140
CCCCACTTTG CGCCGGTGCC TTTGCCCCAG CGGAGCCTGC TTCGCCATCT CCGAGCCCCA CCGCCCCTCC 150        160        170        180        190        200        210
ACTCCTCGGC CTTGCCCGAC ACTGAGACGC TGTTCCCAGC GTGAAAAGAG AGACTGCGCG GCCGGCACCC 220        230        240        250        260        270        280
GGGAGAAGGA GGAGGCAAAG AAAAGGAACG GACATTCGGT CCTTGCGCCA GGTCCTTTGA CCAGAGTTTT 290        300        310        320        330        340        350
TCCATGTGGA CGCTCTTTCA ATGGACGTGT CCCCGCGTGC TTCTTAGACG GACTGCGGTC TCCTAAAGGT
```

```
      (1)               370              385                 400
CGACC ATG GTG GCC GGG ACC CGC TGT CTT CTA GCG TTG CTG CTT CCC CAG GTC
      MET Val Ala Gly Thr Arg Cys Leu Leu Ala Leu Leu Leu Pro Gln Val 415             430              445
CTC CTG GGC GGC GCG GCT GGC CTC GTT CCG GAG CTG GGC CGC AGG AAG TTC GCG
Leu Leu Gly Gly Ala Ala Gly Leu Val Pro Glu Leu Gly Arg Arg Lys Phe Ala 460             475              490             505
GCG GCG TCG TCG GGC CGC CCC TCA TCC CAG CCC TCT GAC GAG GTC CTG AGC GAG
Ala Ala Ser Ser Gly Arg Pro Ser Ser Gln Pro Ser Asp Glu Val Leu Ser Glu 520             535             550             565
TTC GAG TTG CGG CTG CTC AGC ATG TTC GGC CTG AAA CAG AGA CCC ACC CCC AGC
Phe Glu Leu Arg Leu Leu Ser MET Phe Gly Leu Lys Gln Arg Pro Thr Pro Ser 580             595             610
AGG GAC GCC GTG GTG CCC CCC TAC ATG CTA GAC CTG TAT CGC AGG CAC TCA GGT
Arg Asp Ala Val Val Pro Pro Tyr MET Leu Asp Leu Tyr Arg Arg His Ser Gly 625             640             655             670
CAG CCG GGC TCA CCC GCC CCA GAC CAC CGG TTG GAG AGG GCA GCC AGC CGA GCC
Gln Pro Gly Ser Pro Ala Pro Asp His Arg Leu Glu Arg Ala Ala Ser Arg Ala 685             700             715
AAC ACT GTG CGC AGC TTC CAC CAT GAA GAA TCT TTG GAA GAA CTA CCA GAA ACG
Asn Thr Val Arg Ser Phe His His Glu Glu Ser Leu Glu Glu Leu Pro Glu Thr
```

FIGURE 2A

```
730                 745                 760                 775
AGT GGG AAA ACA ACC CGG AGA TTC TTC TTT AAT TTA AGT TCT ATC CCC ACG GAG
Ser Gly Lys Thr Thr Arg Arg Phe Phe Phe Asn Leu Ser Ser Ile Pro Thr Glu 790                 805                 820                 835
GAG TTT ATC ACC TCA GCA GAG CTT CAG GTT TTC CGA GAA CAG ATG CAA GAT GCT
Glu Phe Ile Thr Ser Ala Glu Leu Gln Val Phe Arg Glu Gln MET Gln Asp Ala 850                 865                 880
TTA GGA AAC AAT AGC AGT TTC CAT CAC CGA ATT AAT ATT TAT GAA ATC ATA AAA
Leu Gly Asn Asn Ser Ser Phe His His Arg Ile Asn Ile Tyr Glu Ile Ile Lys 895                 910                 925                 940
CCT GCA ACA GCC AAC TCG AAA TTC CCC GTG ACC AGA CTT TTG GAC ACC AGG TTG
Pro Ala Thr Ala Asn Ser Lys Phe Pro Val Thr Arg Leu Leu Asp Thr Arg Leu 955                 970                 985
GTG AAT CAG AAT GCA AGC AGG TGG GAA AGT TTT GAT GTC ACC CCC GCT GTG ATG
Val Asn Gln Asn Ala Ser Arg Trp Glu Ser Phe Asp Val Thr Pro Ala Val MET 1000                1015                1030                1045
CGG TGG ACT GCA CAG GGA CAC GCC AAC CAT GGA TTC GTG GTG GAA GTG GCC CAC
Arg Trp Thr Ala Gln Gly His Ala Asn His Gly Phe Val Val Glu Val Ala His 1060                1075                1090                1105
TTG GAG GAG AAA CAA GGT GTC TCC AAG AGA CAT GTT AGG ATA AGC AGG TCT TTG
Leu Glu Glu Lys Gln Gly Val Ser Lys Arg His Val Arg Ile Ser Arg Ser Leu 1120                1135                1150
CAC CAA GAT GAA CAC AGC TGG TCA CAG ATA AGG CCA TTG CTA GTA ACT TTT GGC
His Gln Asp Glu His Ser Trp Ser Gln Ile Arg Pro Leu Leu Val Thr Phe Gly 1165                1180                1195                1210
CAT GAT GGA AAA GGG CAT CCT CTC CAC AAA AGA GAA AAA CGT CAA GCC AAA CAC
His Asp Gly Lys Gly His Pro Leu His Lys Arg Glu Lys Arg Gln Ala Lys His 1225                1240              (299)1255
AAA CAG CGG AAA CGC CTT AAG TCC AGC TGT AAG AGA CAC CCT TTG TAC GTG GAC
Lys Gln Arg Lys Arg Leu Lys Ser Ser Cys Lys Arg His Pro Leu Tyr Val Asp 1270                1285                1300                1315
TTC AGT GAC GTG GGG TGG AAT GAC TGG ATT GTG GCT CCC CCG GGG TAT CAC GCC
Phe Ser Asp Val Gly Trp Asn Asp Trp Ile Val Ala Pro Pro Gly Tyr His Ala 1330                1345                1360                1375
TTT TAC TGC CAC GGA GAA TGC CCT TTT CCT CTG GCT GAT CAT CTG AAC TCC ACT
Phe Tyr Cys His Gly Glu Cys Pro Phe Pro Leu Ala Asp His Leu Asn Ser Thr 1390                1405                1420
AAT CAT GCC ATT GTT CAG ACG TTG GTC AAC TCT GTT AAC TCT AAG ATT CCT AAG
Asn His Ala Ile Val Gln Thr Leu Val Asn Ser Val Asn Ser Lys Ile Pro Lys
```

FIGURE 2B

```
   1435                1450                1465                1480
GCA TGC TGT GTC CCG ACA GAA CTC AGT GCT ATC TCG ATG CTG TAC CTT GAC GAG
Ala Cys Cys Val Pro Thr Glu Leu Ser Ala Ile Ser MET Leu Tyr Leu Asp Glu 1495                1510                1525
AAT GAA AAG GTT GTA TTA AAG AAC TAT CAG GAC ATG GTT GTG GAG GGT TGT GGG
Asn Glu Lys Val Val Leu Lys Asn Tyr Gln Asp MET Val Val Glu Gly Cys Gly

1540(396)     1553      1563       1573       1583       1593       1603
TGT CGC TAGTACAGCA AAATTAAATA CATAAATATA TATATATATA TATATTTTAG AAAAAAGAAA
Cys Arg
```

AAAA

FIGURE 3

```
         10         20         30         40         50         60         70
CTCTAGAGGG CAGAGGAGGA GGGAGGGAGG GAAGGAGCGC GGAGCCCGGC CCGGAAGCTA GGTGAGTGTG 80         90        100        110        120        130        140
GCATCCGAGC TGAGGGACGC GAGCCTGAGA CGCCGCTGCT GCTCCGGCTG AGTATCTAGC TTGTCTCCCC 150        160        170        180        190        200        210
GATGGGATTC CCGTCCAAGC TATCTCGAGC CTGCAGCGCC ACAGTCCCCG GCCCTCGCCC AGGTTCACTG 220        230        240        250        260        270        280
CAACCGTTCA GAGGTCCCCA GGAGCTGCTG CTGGCGAGCC CGCTACTGCA GGGACCTATG GAGCCATTCC 290        300        310        320        330        340        350
GTAGTGCCAT CCCGAGCAAC GCACTGCTGC AGCTTCCCTG AGCCTTTCCA GCAAGTTTGT TCAAGATTGG 360        370        380        390        400      (1)
CTGTCAAGAA TCATGGACTG TTATTATATG CCTTGTTTTC TGTCAAGACA CC ATG ATT CCT
                                                          MET Ile Pro
```

```
    417                         432                         447                         462
GGT AAC CGA ATG CTG ATG GTC GTT TTA TTA TGC CAA GTC CTG CTA GGA GGC GCG
Gly Asn Arg MET Leu MET Val Val Leu Leu Cys Gln Val Leu Leu Gly Gly Ala 477                         492                         507
AGC CAT GCT AGT TTG ATA CCT GAG ACG GGG AAG AAA AAA GTC GCC GAG ATT CAG
Ser His Ala Ser Leu Ile Pro Glu Thr Gly Lys Lys Lys Val Ala Glu Ile Gln 522                         537                         552                         567
GGC CAC GCG GGA GGA CGC CGC TCA GGG CAG AGC CAT GAG CTC CTG CGG GAC TTC
Gly His Ala Gly Gly Arg Arg Ser Gly Gln Ser His Glu Leu Leu Arg Asp Phe 582                         597                         612                         627
GAG GCG ACA CTT CTG CAG ATG TTT GGG CTG CGC CGC CGC CCG CAG CCT AGC AAG
Glu Ala Thr Leu Leu Gln MET Phe Gly Leu Arg Arg Arg Pro Gln Pro Ser Lys 642                         657                         672
AGT GCC GTC ATT CCG GAC TAC ATG CGG GAT CTT TAC CGG CTT CAG TCT GGG GAG
Ser Ala Val Ile Pro Asp Tyr MET Arg Asp Leu Tyr Arg Leu Gln Ser Gly Glu 687                         702                         717                         732
GAG GAG GAA GAG CAG ATC CAC AGC ACT GGT CTT GAG TAT CCT GAG CGC CCG GCC
Glu Glu Glu Glu Gln Ile His Ser Thr Gly Leu Glu Tyr Pro Glu Arg Pro Ala
```

FIGURE 3A

```
         747                    762                    777
AGC CGG GCC AAC ACC GTG AGG AGC TTC CAC CAC GAA GAA CAT CTG GAG AAC ATC
Ser Arg Ala Asn Thr Val Arg Ser Phe His His Glu Glu His Leu Glu Asn Ile 792                    807                    822                    837
CCA GGG ACC AGT GAA AAC TCT GCT TTT CGT TTC CTC TTT AAC CTC AGC AGC ATC
Pro Gly Thr Ser Glu Asn Ser Ala Phe Arg Phe Leu Phe Asn Leu Ser Ser Ile 852                    867                    882                    897
CCT GAG AAC GAG GTG ATC TCC TCT GCA GAG CTT CGG CTC TTC CGG GAG CAG GTG
Pro Glu Asn Glu Val Ile Ser Ser Ala Glu Leu Arg Leu Phe Arg Glu Gln Val 912                    927                    942
GAC CAG GGC CCT GAT TGG GAA AGG GGC TTC CAC CGT ATA AAC ATT TAT GAG GTT
Asp Gln Gly Pro Asp Trp Glu Arg Gly Phe His Arg Ile Asn Ile Tyr Glu Val 957                    972                    987                    1002
ATG AAG CCC CCA GCA GAA GTG GTG CCT GGG CAC CTC ATC ACA CGA CTA CTG GAC
MET Lys Pro Pro Ala Glu Val Val Pro Gly His Leu Ile Thr Arg Leu Leu Asp 1017                   1032                   1047
ACG AGA CTG GTC CAC CAC AAT GTG ACA CGG TGG GAA ACT TTT GAT GTG AGC CCT
Thr Arg Leu Val His His Asn Val Thr Arg Trp Glu Thr Phe Asp Val Ser Pro 1062                   1077                   1092                   1107
GCG GTC CTT CGC TGG ACC CGG GAG AAG CAG CCA AAC TAT GGG CTA GCC ATT GAG
Ala Val Leu Arg Trp Thr Arg Glu Lys Gln Pro Asn Tyr Gly Leu Ala Ile Glu 1122                   1137                   1152                   1167
GTG ACT CAC CTC CAT CAG ACT CGG ACC CAC CAG GGC CAG CAT GTC AGG ATT AGC
Val Thr His Leu His Gln Thr Arg Thr His Gln Gly Gln His Val Arg Ile Ser 1182                   1197                   1212
CGA TCG TTA CCT CAA GGG AGT GGG AAT TGG GCC CAG CTC CGG CCC CTC CTG GTC
Arg Ser Leu Pro Gln Gly Ser Gly Asn Trp Ala Gln Leu Arg Pro Leu Leu Val 1227                   1242                   1257                   1272
ACC TTT GGC CAT GAT GGC CGG GGC CAT GCC TTG ACC CGA CGC CGG AGG GCC AAG
Thr Phe Gly His Asp Gly Arg Gly His Ala Leu Thr Arg Arg Arg Arg Ala Lys 1287                   1302                   1317
CGT AGC CCT AAG CAT CAC TCA CAG CGG GCC AGG AAG AAG AAT AAG AAC TGC CGG
Arg Ser Pro Lys His His Ser Gln Arg Ala Arg Lys Lys Asn Lys Asn Cys Arg

1332(311)              1347                   1362                   1377
CGC CAC TCG CTC TAT GTG GAC TTC AGC GAT GTG GGC TGG AAT GAC TGG ATT GTG
Arg His Ser Leu Tyr Val Asp Phe Ser Asp Val Gly Trp Asn Asp Trp Ile Val 1392                   1407                   1422                   1437
GCC CCA CCA GGC TAC CAG GCC TTC TAC TGC CAT GGG GAC TGC CCC TTT CCA CTG
Ala Pro Pro Gly Tyr Gln Ala Phe Tyr Cys His Gly Asp Cys Pro Phe Pro Leu
```

FIGURE 3B

```
           1452                1467                1482
GCT GAC CAC CTC AAC TCA ACC AAC CAT GCC ATT GTG CAG ACC CTG GTC AAT TCT
Ala Asp His Leu Asn Ser Thr Asn His Ala Ile Val Gln Thr Leu Val Asn Ser 1497                1512                1527                1542
GTC AAT TCC AGT ATC CCC AAA GCC TGT TGT GTG CCC ACT GAA CTG AGT GCC ATC
Val Asn Ser Ser Ile Pro Lys Ala Cys Cys Val Pro Thr Glu Leu Ser Ala Ile 1557                1572                1587
TCC ATG CTG TAC CTG GAT GAG TAT GAT AAG GTG GTA CTG AAA AAT TAT CAG GAG
Ser MET Leu Tyr Leu Asp Glu Tyr Asp Lys Val Val Leu Lys Asn Tyr Gln Glu 1602                1617         (408)    1636          1646        1656
ATG GTA GTA GAG GGA TGT GGG TGC CGC TGAGATCAGG CAGTCCTTGA GGATAGACAG
MET Val Val Glu Gly Cys Gly Cys Arg 1666       1676       1686       1696       1706       1716       1726
ATATACACAC CACACACACA CACCACATAC ACCACACACA CACGTTCCCA TCCACTCACC CACACACTAC 1736       1746       1756       1766       1776       1786       1796
ACAGACTGCT TCCTTATAGC TGGACTTTTA TTTAAAAAAA AAAAAAAAAA AATGGAAAAA ATCCCTAAAC 1806       1816       1826       1836       1846       1856       1866
ATTCACCTTG ACCTTATTTA TGACTTTACG TGCAAATGTT TTGACCATAT TGATCATATA TTTTGACAAA 1876       1886       1896       1906       1916       1926       1936
ATATATTTAT AACTACGTAT TAAAAGAAAA AAATAAAATG AGTCATTATT TTAAAAAAAA AAAAAAAACT

1946
CTAGAGTCGA CGGAATTC
```

COMPOSITIONS COMPRISING BONE MORPHOGENETIC PROTEIN-2 (BMP-2)

CROSS-REFERENCE TO RELATED APPLICATIONS

This application is a continuation of U.S. Ser. No. 884,353 filed May 18, 1992, now abandoned, which is a divisional of U.S. Ser. No. 378,537 filed Jul. 11, 1989, now U.S. Pat. No. 5,166,058, which is a continuation-in-part of U.S. Ser. No. 179,100, now U.S. Pat. No. 5,013,649, filed Apr. 8, 1988, which is a continuation-in-part of U.S. Ser. No. 028,285 filed Mar. 20, 1987, now abandoned, which is a continuation-in-part of U.S. Ser. Nos. 943,332 filed Dec. 17, 1986, now abandoned, which is a continuation-in-part of U.S. Ser. No. 880,776 filed Jul. 1, 1986, now abandoned.

The present invention relates to a novel family of purified proteins designated BMP-2 (wherein BMP is bone morphogenic protein) proteins and processes for obtaining them. These proteins may be used to induce bone and/or cartilage formation and in wound healing and tissue repair.

Human BMP-2 proteins are produced by culturing a cell transformed with a cDNA substantially as shown in Table II or Table III and recovering from the culture medium a protein containing the 97 amino acid sequence #299 to #396 of Table II or amino acid #311 to #408 of Table III, respectively.

BMP-2 proteins are further characterized by the ability to induce the formation of cartilage and/or bone. Members of the BMP-2A protein family may be further characterized by the ability to demonstrate cartilage and/or bone formation activity in the rat bone formation assay described below. In preferred embodiments, the proteins of the invention demonstrate activity in this rat bone formation assay at a concentration of 0.5 µg –100 µg/gram of bone. In more preferred embodiments these proteins demonstrate activity in this assay at a concentration of 1 µg–50 µg/gram of bone. More particularly, these proteins may be characterized by the ability of 1 µg of the protein to score at least +1 in the rat bone formation assay described in Example III using the modified scoring described in Example VII.

BMP-2A is a member of the family of the BMP-2 proteins of the invention. We have previously referred to BMP-2A as BMP-2 or BMP-2 Class I. Human BMP-2A (or hBMP-2A) is produced by culturing a cell transformed with a cDNA comprising the nucleotide sequence from nucleotide #356 to #1543 as shown in Table II and recovering and purifying from the culture medium a protein containing the amino acid sequence of amino acid #299 to amino acid #396 as shown in Table II, substantially free from other proteinaceous materials with which it is co-produced. Human BMP-2A is further characterized by the ability to induce cartilage formation. Human BMP-2A is further characterized by the ability to induce bone formation. Human BMP-2A may be further characterized by the ability to demonstrate cartilage and/or bone formation activity in the rat bone formation assay described below. In preferred embodiments, the proteins of the invention demonstrate activity in this rat bone formation assay at a concentration of 0.5 µg–100 µg/gram of bone. In more preferred embodiments these proteins demonstrate activity in this assay at a concentration of 1 µg–50 µg/gram of bone. More particularly, these proteins may be characterized by the ability of 1 µg of the protein to score at least +1 in the rat bone formation assay of Example III using the modified scoring method described in Example VII.

The bovine BMP-2A protein is a member of the family of BMP-2 proteins of the invention. It contains substantially the amino acid sequence represented by amino acid #32 to amino acid #129 of Table I. These proteins are capable of inducing the formation of cartilage and/or bone. Bovine BMP-2A may be further characterized by the ability to demonstrate cartilage and/or bone formation activity in the rat bone formation assay described below. In preferred embodiments, the proteins of the invention demonstrate activity in this rat bone formation assay at a concentration of 0.5 µg –100 µg/gram of bone. In more preferred embodiments these proteins demonstrate activity in this assay at a concentration of 1 µg–50 µg/gram of bone. More particularly, these proteins may be characterized by the ability of 1 µg of the protein to score at least +1 in the rat bone formation assay described in Example III using the modified scoring method as described in Example VII.

Another member of the BMP-2 protein family is designated BMP-2B and which we have previously referred to as BMP-4 or BMP-2 Class II. BMP-2B is produced by culturing a cell transformed with a cDNA substantially as shown in Table III and recovering and purifying from the culture medium a protein containing the amino acid sequence from amino acid #311 to #408 as shown in Table III substantially free from other proteinaceous materials with which it is co-produced. These proteins are capable of inducing formation of cartilage and/or bone. BMP-2B is further characterized by the ability to demonstrate cartilage and/or bone formation activity in the rat bone formation assay described below. In preferred embodiments, the proteins of the invention demonstrate activity in this rat bone formation assay at a concentration of 0.5 µg –100 µg/gram of bone. In more preferred embodiments these proteins demonstrate activity in this assay at a concentration of 1 µg–50 µg/gram of bone. More particularly, these proteins may be characterized by the ability of 1 µg of the protein to score at least +1 in the rat bone formation assay of Example III using the modified scoring method described in Example VII.

Another aspect of the invention provides pharmaceutical compositions containing a therapeutically effective amount of a BMP-2 protein in a pharmaceutically acceptable vehicle or carrier. BMP-2 compositions may also be used for wound healing and tissue repair. The invention further provides pharmaceutical compositions containing a therapeutically effective amount of BMP-2A or BMP-2B in a pharmaceutically acceptable vehicle. Further compositions may contain both BMP-2A and BMP-2B in a pharmaceutically acceptable vehicle. Compositions of the invention may further include at least one other therapeutically useful agent such as the BMP proteins BMP-1, BMP-3, BMP-5, BMP-6 and BMP-7, disclosed respectively in co-owned U.S. patent applications Ser. No. 179,101, now abandoned, Ser. No. 179,197, now abandoned, Ser. No. 370,547, now U.S. Pat. No. 5,106,748, Ser. No. 370,544, now abandoned, and Ser. No. 370,549, now abandoned. Other therapeutically useful agents include growth factors such as epidermal growth factor (EGF), fibroblast growth factor (FGF), and transforming growth factor (TGF-a and TGF-b). The compositions may also include an appropriate matrix for instance, for supporting the composition and providing a surface for bone and/or cartilage growth. The compositions may be employed in methods for treating a number of bone and/or cartilage defects, periodontal disease and various types of wounds. These methods, according to the invention, entail administering to a patient needing such bone and/or cartilage formation wound healing or tissue repair, an effective amount of a BMP-2 protein such as BMP-2A and/or BMP-2B. These methods may also entail the administration of a protein of the invention in conjunction with at least one of the novel BMP proteins disclosed in the co-owned applications described above. In addition, these methods may also include the administration of a BMP-2 protein with other growth factors.

Still a further aspect of the invention are DNA sequences coding on expression for a BMP-2 protein. Such sequences include the sequence of nucleotides in a 5' to 3' direction illustrated in Tables I through III or DNA sequences which hybridize under stringent conditions with the DNA sequences of Tables I–III and encode a protein having the ability to induce the formation of cartilage and/or bone. Finally, allelic or other variations of the sequences of Tables I through III, whether such nucleotide changes result in changes in the peptide sequence or not, are also included in the present invention.

Still a further aspect of the invention is a vector Containing a DNA sequence as described above in operative association with an expression control sequence therefor. Such vector may be employed in a novel process for producing a BMP-2 protein of the invention in which a cell line transformed with a DNA sequence encoding expression of a BMP-2 protein in operative association with an expression control sequence therefor, is cultured in a suitable culture medium and a BMP-2 protein is isolated and purified therefrom. This claimed process may employ a number of known cells both prokaryotic and eukaryotic as host cells for expression of the polypeptide.

Other aspects and advantages of the present invention will be apparent upon consideration of the following detailed description and preferred embodiments thereof.

BRIEF DESCRIPTION OF THE DRAWING

FIG. 1 comprises partial DNA sequence and derived amino acid sequence of bovine BMP-2 (BMP-2A) from bacteriophage bP-21 ATCC #40310. FIG. 1 corresponds to Table I further described below.

FIG. 2 comprises DNA sequence and derived amino acid sequence of human BMP-2 (BMP-2A) from lambda U2OS-39 ATCC #40345. FIG. 2 corresponds to Table II further described below.

FIG. 3 comprises DNA sequence and derived amino acid sequence of human BMP-4 (BMP-2B) from lambda U2OS-3 ATCC #40342. FIG. 3 corresponds to Table III further described below.

DETAILED DESCRIPTION OF THE INVENTION

The purified human BMP-2 proteins of the present invention are produced by culturing a host cell transformed with a cDNA of Table II (for the production of BMP-2A) or III (for the production of BMP-2B) and recovering from the culture medium a protein which contains the 97 amino acid sequence or a substantially homologous sequence as represented by amino acid #299 to #396 of Table II or contains the amino acid sequence from amino acid #311 to #408 of Table III, respectively. BMP-2 proteins may be further characterized by the ability to induce the formation of cartilage. BMP-2 proteins may be further characterized by the ability to induce the formation of bone. Some BMP-2 proteins may be further characterized by the ability to demonstrate cartilage and/or bone formation activity in the rat bone formation assay described below. In preferred embodiments, the proteins of the invention demonstrate activity in this rat bone formation assay at a concentration of 0.5 µg–100 µg/gram of bone. In more preferred embodiments these proteins demonstrate activity in this assay at a concentration of 1 µg–50 µg/gram of bone. More particularly, these proteins may be characterized by the ability of 1 µg of the protein to score at least +2 in the rat bone formation assay.

The BMP-2 proteins provided herein also include factors encoded by the sequences similar to those of Tables I–III, but into which modifications are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of Tables I–III. These sequences, by virtue of sharing primary, secondary, or tertiary structural and conformational characteristics with bone growth factor polypeptides of Tables I–III may possess bone growth factor biological properties in common therewith. Thus, they may be employed as biologically active substitutes for naturally-occurring BMP-2A and BMP-2B and other BMP-2 polypeptides in therapeutic processes.

Other specific mutations of the sequences of BMP-2 proteins described herein involve modifications of at least one of the glycosylation sites. The absence of glycosylation or only partial glycosylation results from amino acid substitution or deletion at asparagine-linked glycosylation recognition sites present in the sequences of BMP-2A and BMP-2B proteins shown in Tables I–III. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of/amino acid substitutions or deletions at one or both of the first or third amino acid positions of a glycosylation recognition site (and/or amino acid deletion at the second position) results in non-glycosylation at the modified tripeptide sequence.

The present invention also encompasses the novel DNA sequences, free of association with DNA sequences encoding other proteinaceous materials, and coding on expression for BMP-2 proteins such as BMP-2A and BMP-2B. These DNA sequences include those depicted in Tables I -III in a 5' to 3' direction and those sequences which hybridize under stringent hybridization conditions [see, T. Maniatis et al, *Molecular Cloning (A Laboratory Manual)*, Cold Spring Harbor Laboratory (1982), pages 387 to 389] to the DNA sequences of Tables I–III.

Similarly, DNA sequences which code for BMP-2 proteins such as BMP-2A and BMP-2B polypeptides coded for by the sequences of Tables I–III, but which differ in codon sequence due to the degeneracies of the genetic code or allelic variations (naturally-occurring base changes in the species population which may or may not result in an amino acid change) also encode the novel factors described herein. Variations in the DNA sequences of Tables I–III which are caused by point mutations or by induced modifications (including insertion, deletion, and substitution) to enhance the activity, half-life or production of the polypeptides encoded thereby are also encompassed in the invention.

Another aspect of the present invention provides a novel method for producing BMP-2 proteins. The method of the present invention involves culturing a suitable cell line, which has been transformed with a DNA sequence coding on expression for a BMP-2 protein of the invention, under the control of known regulatory sequences. Suitable cells or cell lines may be mammalian cells, such as Chinese hamster ovary cells (CHO). The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of E. coli (e.g., HB101, MC1061) are well-known as host cells in the field of biotechnology. Various strains of *B. subtilis, Pseudomonas,* other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of these novel BMP-2 polypeptides. Preferably the vectors contain the full novel DNA sequences described above which code for the novel factors of the invention. Additionally the vectors also contain appropriate expression control sequences permitting expression of the BMP-2 protein sequences. Alternatively, vectors incorporating modified sequences as described above are also embodiments of the present invention and useful in the production of the BMP-2A and BMP-2B and other BMP-2 proteins. The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to one of skill in the art and may be selected depending upon the selected host cells. Such selection is routine and does not form part of the present invention.

A protein of the present invention, which induces cartilage and/or bone growth in circumstances where bone is not normally formed, has application in the healing of bone fractures and cartilage defects in humans and other animals. Such a preparation employing a BMP-2 protein such as BMP-2A and BMP-2B may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A BMP-2 protein may be used in the treatment of periodontal disease, and in other tooth repair processes. Such agents may provide an environment to attract bone-forming cells, stimulate growth of bone-forming cells or induce differentiation of progenitors of bone-forming cells. BMP-2 polypeptides of the invention may also be useful in the treatment of osteoporosis. A variety of osteogenic, cartilage-inducing and bone inducing factors have been described. See, e.g. European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair).

A further aspect of the invention is a therapeutic method and composition for repairing fractures and other conditions related to cartilage and/or bone defects or periodontal diseases. In addition, the invention comprises therapeutic methods and compositions for wound healing and tissue repair. Such compositions comprise a therapeutically effective amount of at least one of the BMP-2 proteins of the invention in admixture with a pharmaceutically acceptable vehicle, carrier or matrix. It is expected that the proteins of the invention may act in concert with or perhaps synergistically with other related proteins and growth factors. Further therapeutic methods and compositions of the invention therefore comprise a therapeutic amount of at least one BMP-2 protein of the invention with a therapeutic amount of at least one of the other BMP proteins disclosed in co-owned and concurrently filed U.S. applications described above. Such combinations may comprise separate molecules of the BMP proteins or heteromolecules comprised of different BMP moieties. For example, a method and composition of the invention may comprise a disulfide linked dimer comprising a BMP-2 protein and another "BMP" protein described above. Further, BMP-2 proteins such as BMP-2A and BMP-2B may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-a and TGF-b), and insulin-like growth factor (IGF). The preparation and formulation of such physiologically acceptable protein compositions, having due regard to pH, isotonicity, stability and the like, is within the skill of the art. The therapeutic compositions are also presently valuable for veterinary applications due to the lack of species specificity in BMP proteins. Particularly domestic animals and thoroughbred horses in addition to humans are desired patients for such treatment with BMP-2A and BMP-2B of the present invention.

BMP-2A may be used individually in a pharmaceutical composition. BMP-2A may also be used in combination with BMP-2B and/or one or more of the other BMP proteins disclosed in co-owned and co-pending U.S. applications as discussed above.

BMP-2B may be used individually in pharmaceutical composition. In addition, it may be used in combination with other BMP proteins as described above.

The therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone cartilage or tissue damage. Topical administration may be suitable for wound healing and tissue repair. Preferably for bone and/or cartilage formation, the composition would include a matrix capable of delivering BMP-2A, BMP-2B or other BMP protein to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the BMP-2 compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular .matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphateo The bioceramics may be altered in composition, such as in calcium-aluminate-phosphate and processing to alter pore size, particle size, particle shape, and biodegradability.

The dosage regimen will be determined by the attending physician considering various factors which modify the action of the BMP-2 protein, e.g. amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the types of BMP proteins in the composition. The addition of other known growth factors, such as IGF I (insulin like growth factor I), to the final composition, may also affect the dosage. Progress can be monitored by periodic assessment of bone growth and/or repair, for example, x-rays, histomorphometric determinations and tetracycline labeling.

The following examples illustrate practice of the present invention in recovering and characterizing bovine BMP-2A protein and employing it to recover the human proteins BMP-2A and BMP-2B, obtaining the human proteins and in expressing the proteins via recombinant techniques.

EXAMPLE I

Isolation of Bovine Bone Inductive Factor

Ground bovine bone powder (20–120 mesh, Helitrex) is prepared according to the procedures of M. R. Urist et al., *Proc. Natl Acad. Sci USA*, 70:3511 (1973) with elimination of some extraction steps as identified below. Ten kgs of the ground powder is demineralized in successive changes, of 0.6N HCl at 4° C. over a 48 hour period with vigorous stirring. The resulting suspension is extracted for 16 hours at 4° C. with 50 liters of 2M $CaCl_2$ and 10 mM ethylenediamine-tetraacetic acid [EDTA], and followed by extraction for 4 hours in 50 liters of 0.5M EDTA. The residue is washed three times with distilled water before its resuspension in 20 liters of 4M guanidine hydrochloride [GuCl], 20 mM Tris (pH 7.4), 1 mM N-ethylmaleimide, 1 mM iodoacetamide, 1 mM phenylmethylsulfonyl fluorine as described in *Clin. Orthop. Rel. Res.*, 171: 213 (1982). After 16 to 20 hours the supernatant is removed and replaced with another 10 liters of GuCl buffer. The residue is extracted for another 24 hours.

The crude GuCl extracts are combined, concentrated approximately 20 times on a Pellicon apparatus with a 10,000 molecular weight cut-off membrane, and then dialyzed in 50 mM Tris, 0.1M NaCl, 6M urea (pH 7.2), the starting buffer for the first column. After extensive dialysis the protein is loaded on a 4 liter DEAE cellulose column and the unbound fractions are collected.

The unbound fractions are concentrated and dialyzed against 50 mM NaAc, 50 mM NaCl (pH 4.6) in 6M urea. The unbound fractions are applied to a carboxymethyl cellulose column. Protein not bound to the column is removed by extensive washing with starting buffer, and the material containing protein having bone and/or cartilage formation activity as measured by the Rosen-modified Sampath—Reddi assay (described in Example III below) desorbed from the column by 50 mM NaAc, 0.25 mM NaCl, 6M urea (pH 4.6). The protein from this step elution is concentrated 20- to 40- fold, then diluted 5 times with 80 mM $KPO_4$, 6M urea (pH6.0). The pH of the solution is adjusted to 6.0 with 500 mM $K_2HPO_4$. The sample is applied to an hydroxylapatite column (LKB) equilibrated in 80 mM $KPO_4$, 6M urea (pH 6.0) and all unbound protein is removed by washing the column with the same buffer. Protein having bone and/or cartilage formation activity is eluted with 100 mM $KPO_4$ (pH 7.4) and 6M urea.

The protein is concentrated approximately 10 times, and solid NaCl added to a final concentration of 0.15M. This material is applied to a heparin—Sepharose column equilibrated in 50 mM $KPO_4$, 150mM NaCl, 6M urea (pH 7.4). After extensive washing of the column with starting buffer, a protein with bone and/or cartilage inductive activity is eluted by 50 mM $KPO_4$, 700 mM NaCl, 6M urea (pH 7.4). This fraction is concentrated to a minimum volume, and 0.4 ml aliquots are applied to Superose 6 and Superose 12 columns connected in series, equilibrated with 4M GuCl, 20 mM Tris (pH 7.2) and the columns developed at a flow rate of 0.25 ml/min. The protein demonstrating bone and/or cartilage inductive activity has a relative migration on SDS-PAGE corresponding to approximately 30,000 dalton protein.

The above fractions from the superose columns are pooled, dialyzed against 50 mM NaAc, 6M urea (pH 4.6), and applied to a Pharmacia MonoS HR column. The column is developed with a gradient to 1.0 M NaCl, 50 mM NaAc, 6M urea (pH 4:6). Active bone and/or cartilage formation fractions are pooled and brought to pH3.0 with 10% trifluoroacetic acid (TFA). The material is applied to a 0.46× 25cm Vydac C4 column in 0.1% TFA and the column developed with a gradient to 90% acetonitrile, 0.1% TFA (31.5% acetonitrile, 0.1% TFA to 49.5% acetonitrile, 0.1% TFA in 60 minutes at 1 ml per minute). Active material is eluted at approximately 40–44% acetonitrile. Aliquots of the appropriate active fractions are iodinated by one of the following methods: P. J. McConahey et al, *Int. Arch. Allergy*, 29:185–189 (1966); A. E. Bolton et al, *Biochem J.*, 133:529 (1973); and D. F. Bowen-Pope, *J. Biol. Chem.*, 237:5161 (1982). The iodinated proteins present in these fractions are analyzed by SDS gel electrophoresis and urea Triton X 100 isoelectric focusing. At this stage, the protein having bone and/or cartilage forming activity is estimated to be approximately 10–50% pure.

EXAMPLE II

Characterization of Bovine Bone Inductive Factor

A. Molecular Weight

Approximately 20 ug protein from Example I is lyophilized and redissolved in 1X SDS sample buffer. After 15 minutes of heating at 37° C., the sample is applied to a 15% SDS polyacrylamide gel and then electrophoresed with cooling. The molecular weight is determined relative to prestained molecular weight standards (Bethesda Research Labs). Immediately after completion, the gel lane containing bone and/or cartilage forming material is sliced into 0.3 cm pieces. Each piece is mashed and 1.4 ml of 0.1% SDS is added. The samples are shaken gently overnight at room temperature to elute the protein. Each gel slice is desalted to prevent interference in the biological assay. The supernatant from each sample is acidified to pH 3.0 with 10% TFA, filtered through a 0.45 micron membrane and loaded on a 0.46 cm×5cm C4 Vydac column developed with a gradient of 0.1% TFA to 0.1% TFA, 90% $CH_3CN$. The appropriate bone and/or cartilage inductive protein—containing fractions are pooled and reconstituted with 20 mg rat matrix and assayed. In this gel system, the majority of bone and/or cartilage inductive fractions have the mobility of a protein having a molecular weight of approximately 28,000–30,000 daltons.

B. Isoelectric Focusing

The isoelectric point of bone inductive factor activity is determined in a denaturing isoelectric focusing system. The Triton X100 urea gel system (Hoeffer Scientific) is modified as follows: 1) 40% of the ampholytes used are Servalyte 3/10; 60% are Servalyte 7–9; and 2) the catholyte used is 40 mM NaOH. Approximately 20ug of protein from Example I is lyophilized, dissolved in sample buffer and applied to-the isoelectrofocusing gel. The gel is run at 20 watts, 10° C. for approximately 3 hours. At completion the lane containing bone and/or cartilage inductive factor is sliced into 0.5 cm slices. Each piece is mashed in 1.0 ml 6M urea, 5 mM Tris (pH 7.8) and the samples agitated at room temperature. The samples are acidified, filtered, desalted and assayed as described above. The major portion of activity as determined by the Rosen-modified Sampath—Reddi assay migrates in a manner consistent with a pI of about 8.8–9.2.

C. Subunit Characterization

The subunit composition of the isolated bovine bone protein is also determined. Pure bone inductive factor is isolated from a preparative 15% SDS gel as described above. A portion of the sample is then reduced with 5 mM DTT in sample buffer and re-electrophoresed on a 15% SDS gel. The approximately 28–30 kd protein yields two major bands at approximately 18–20 kd and approximately 16–18 kd, as well as a minor band at approximately 28–30 kd. The broadness of the two bands indicates heterogeneity caused most probably by glycosylation, other post translational modification, proteolytic degradation or carbamylation.

EXAMPLE III

Rosen Modified Sampath-Reddi Assay

A modified version of the rat bone formation assay described in Sampath and Reddi, *Proc. Natl. Acad. Sci. U.S.A.*, 80:6591–6595 (1983) is used to evaluate bone and/or cartilage activity of the bovine protein obtained in Example I and the BMP-1 proteins of the invention. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1% TFA, and the resulting solution added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatase analysis [See, A. H. Reddi et al., *Proc. Natl Acad Sci.*, 69:1601 (1972)].

The other half of each implant is fixed and processed for histological analysis. About 1 um glycolmethacrylate sections are stained with Von Kossa and acid fuschin to score the amount of induced bone and cartilage formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone.

The rat matrix samples containing at least 200 ng of protein obtained in Example I result in bone and/or cartilage formation that filled more than 20% of the implant areas that was sectioned for histology. This protein therefore scores at least +2 in the Rosen-modified Sampath-Reddi assay. The dose response of the matrix samples indicates that the amount of bone and/or cartilage formed increases with the amount of protein in the sample. The control sample did not result in any bone and/or cartilage formation. The purity of the protein assayed is approximately 10–15% pure.

The bone and/or cartilage formed is physically confined to the space occupied by the matrix. Samples are also analyzed by SDS gel electrophoresis and isoelectric focusing as described above, followed by autoradiography. Analysis reveals a correlation of activity with protein bands at 28–30 kd and a pI of approximately 8.8–9.2. To estimate the purity of the protein in a particular fraction an extinction coefficient of 1 OD/mg-cm is used as an estimate for protein and the protein is run on SDS PAGE followed by silver straining or radioiodination and autoradiography.

EXAMPLE IV

Bovine BMP-2A

The protein composition of Example IIA of molecular weight 28–30kd is reduced as described in Example IIC and digested with trypsin. Eight tryptic fragments are isolated by standard procedures having the following amino acid sequences:

Fragment 1: A A F L G D I A L D E E D L G
Fragment 2: A F Q V Q Q A A D L
Fragment 3: N Y Q D M V V E G
Fragment 4: S T P A Q D V S R
Fragment 5: N Q E A L R
Fragment 6: L S E P D P S H T L E E
Fragment 7: F D A Y Y
Fragment 8: L K P S N ? A T I Q S I V E Two probes consisting of pools of oligonucleotides (or unique oligonucleotides) are designed according to the method of R. Lathe, *J. Mol. Biol.*, 183(1):1–12 (1985) on the basis of the amino acid sequence of Fragment 3 and synthesized on an automated DNA synthesizer as described above.

Probe #1: A C N A C C A T [A/G] T C [T/C] T G [A/G] A T

Probe #2: C A [A/G] G A [T/C] A T G G T N G T N G A

Because the genetic code is degenerate (more than one codon can code for the same amino acid), the number of oligonucleotides in a probe pool is reduced based on the frequency of codon usage in eukaryotes, the relative stability of G:T base pairs, and the relative infrequency of the dinucleotide CpG in eukaryotic coding sequences [See J. J. Toote et al, *Nature*, 312:342–347 (1984)]. Bracketed nucleotides are alternatives. "N" means either A, T, C or G. These probes are radioactively labeled and employed to screen a bovine genomic library. The library is constructed as follows: Bovine liver DNA is partially digested with the restriction endonuclease enzyme Sau 3A and sedimented through a sucrose gradient. Size fractionated DNA in the range of 15–30kb is then ligated to the vector lambda J' Bam H1 arms [Mullins et al., Nature, 308:856–858 (1984)]. The library is plated at 8000 recombinants per plate. Duplicate nitrocellulose replicas of the plaques are made and amplified according to a modification of the procedure of Woo et al, Proc. Natl. Acad. Sci. USA, 75:3688–91 (1978). Probe #1 is hybridized to the set of filters in 3M tetramethylammonium chloride (TMAC), 0.1M sodium phosphate pH 6.5, 1 mM EDTA, 5X Denhardts, 0.6% SDS, 100ug/ml salmon sperm DNA at 48 degrees C, and washed in 3M TMAC, 50 mM Tris pH 8.0 at 50 degrees C. These conditions minimize the detection of mismatches to the 17 mer probe pool [see, Wood et al, Proc. Natl. Acad. Sci. USA 82:1585–1588 (1985)].

400,000 recombinants are screened by this procedure. One duplicate positive is plaque purified and the DNA is isolated from a plate lysate of the recombinant bacteriophage designated lambda bP-21. Bacteriophage bP-21 was deposited with the American Type Culture Collection, 12301 Parklawn Drive, Rockville, Md. USA (hereinafter the "ATCC") under accession number ATCC 40310 on Mar. 6, 1987. This deposit as well as the other deposits contained herein meets the requirements of the Budapest Treaty on the International Recognition of the Deposit of Microorganisms for the Purposes of Patent Procedure and Regulations thereunder. The bP-21 clone encodes at least a portion of a bovine BMP-2 protein designated bovine BMP-2A or bBMP-2A.

The oligonucleotide hybridizing region of this BMP-2A clone is localized to an approximately 1.2 kb Sac I restriction fragment which is subcloned into M13 and sequenced by standard techniques. The partial DNA sequence and derived amino acid sequence of this Sac I fragment and the contiguous Hind III-Sac I restriction fragment of bP-21 are shown below in Table I. The BMP-2A peptide sequence from this clone is 129 amino acids in length and is encoded by the DNA sequence from nucleotide #1 through nucleotide #387. The amino acid sequence corresponding to the tryptic fragment isolated from the bovine bone 28 to 30kd material is underlined in Table I. The underlined portion of the sequence corresponds to tryptic Fragment 3 above from which the oligonucleotide probes for BMP-2A are designed. The predicted amino acid sequence indicates that tryptic Fragment 3 is preceded by a basic residue (K) as expected considering the specificity of trypsin. The arginine residue encoded by the CGT triplet is presumed to be the carboxy-terminus of the protein based on the presence of a stop codon (TAG) adjacent to it.

TABLE I

```
(1)              15              30              45
GGC CAC GAT GGG AAA GGA CAC CCT CTC CAC AGA AGA GAA AAG CGG
 G   H   D   G   K   G   H   P   L   H   R   R   E   K   R 60              75              90
CAA GCA AAA CAC AAA CAG CGG AAA CGC CTC AAG TCC AGC TGT AAG
 Q   A   K   H   K   Q   R   K   R   L   K   S   S   C   K

(32)        105             120             135
AGA CAC CCT TTA TAT GTG GAC TTC AGT GAT GTG GGG TGG AAT GAC
 R   H   P   L   Y   V   D   F   S   D   V   G   W   N   D 150             165             180
TGG ATC GTT GCA CCG CCG GGG TAT CAT GCC TTT TAC TGC CAT GGG
 W   I   V   A   P   P   G   Y   H   A   F   Y   C   H   G 195             210             225
GAG TGC CCT TTT CCC CTG GCC GAT CAC CTT AAC TCC ACG AAT CAT
 E   C   P   F   P   L   A   D   H   L   N   S   T   N   H 240             255             270
GCC ATT CTC CAA ACT CTG GTC AAC TCA GTT AAC TCT AAG ATT CCC
 A   I   V   Q   T   L   V   N   S   V   N   S   K   I   P 385             300             315
AAG GCA TGC TGT GTC CCA ACA GAG CTC AGC GCC ATC TCC ATG CTG
 K   A   C   C   V   P   T   E   L   S   A   I   S   M   L 330             345             360
TAC CTT GAT GAG AAT GAG AAG GTG GTA TTA AAG ACC TAT CAG GAC
 Y   L   D   E   N   E   K   V   V   L   K   N   Y   Q   D 375           (129)    397           407
ATG GTT GTC GAG GGT TGT GGG TGT CGT TAGCACAGCA AAATAAAATA
 M   V   V   E   G   C   G   C   R 417          427          437          447          457
TAAATATATA TATATATATA TTAGAAAAAC AGCAAAAAAA TCAAGTTGAC 467          477          487          497          507
ACTTTAATAT TTCCCAATGA AGACTTTATT TATGGAATGG AATGGAGAAA 517          527          537          547          557
AAGAAAAACA CAGCTATTTT GAAAACTATA TTTATATCTA CCGAAAAGAA 567          577          587
GTTGGGAAAA CAAATATTTT AATCAGAGAA TTATT
```

EXAMPLE V

Human BMP-2A and BMP-2B

The HindIII-SacI bovine genomic BMP-2A fragment described in Example IV is subcloned into an M13 vector. A $^{32}$P-labeled single-stranded DNA probe is made from a template preparation of this subclone. This probe is used to screen polyadenylated RNAs from various cell and tissue sources. Polyadenylated RNAs from various cell and tissue sources are electrophoresed on formaldehyde-agarose gels and transferred to nitrocellulose by the method of Toole et al., supra. The probe is then hybridized to the nitrocellulose blot in 50% formamide, 5 X SSC, 0.1% SDS, 40 mM sodium phosphate pH 6.5, 100 ug/ml denatured salmon sperm DNA, and 5 mM vanadyl ribonucleosides at 42° C. overnight and washed at 65° C. in 0.2 X SSC, 0.1% SDS. A hybridizing band corresponding to an mRNA species of approximately 3.8 kb is detected in the lane containing RNA from the human cell line U-2 OS. The HindIII-SacI fragment is labeled with $^{32}$P by nick translation and used to screen the nitrocellulose filter replicas of the above-described U-2 OS cDNA library by hybridization in standard hybridization buffer at 65° overnight followed by washing in 1 X SSC, 0.1% SDS at 65°. Twelve duplicate positive clones are picked and replated for secondaries. Duplicate nitrocellulose replicas are made of the secondary plates and both sets hybridized to the bovine genomic probe as the primary screening was performed. One set of filters is then washed in 1 X SSC, 0.1% SDS; the other in 0.1 X SSC, 0.1% SDS at 65°.

Two classes of hBMP-2 cDNA clones are evident based on strong (4 recombinants) or weak (7 recombinants) hybridization signals under the more stringent washing conditions (0.1 X SSC, 0.1% SDS). All 11 recombinant bacteriophage are plaque purified, small scale DNA preparations made from plate lysates of each, and the inserts subcloned into PSP 65 and into M13 for sequence analysis. Sequence analysis of the strongly hybridizing clones designated hBMP-2A (previously designated BMP-2 and BMP-2 Class I) indicates that they have expensive sequence homology with the sequence given in Table I. These clones are therefore cDNA encoding the human equivalent of the protein encoded by the bBMP-2A gene whose partial sequence is given in Table I. Sequence analysis of the weakly hybridizing recombinants designated hBMP-2B (previously designated BMP-4 and BMP-2 Class II) indicates that they are also quite homologous with the sequence given in Table I at the 3' end of their coding regions, but less so in the more 5' regions. Thus they encode a human protein of similar, though not identical, structure to that above.

Full length human BMP-2A cDNA clones are obtained in the following manner. The 1.5 kb insert of one of the BMP-2B subclones (II-10-1) is isolated and radioactively labeled by nick-translation. One set of the nitrocellulose replicas of the U-2 OS cDNA library screened above (50 filters, corresponding to 1,000,000 recombinant bacteriophage) are rehybridized with this probe under stringent conditions (hybridization at 65° in standard hybridization buffer; washing at 65° in 0.2 X SSC, 0.1% SDS). All recombinants which hybridize to the bovine genomic probe which do not hybridize to the BMP-2B probe are picked and plaque purified (10 recombinants). Plate stocks are made and small scale bacteriophage DNA preparations made. After subcloning into M13, sequence analysis indicates that 4 of these represent clones which overlap the original BMP-2A clone. One of these, lambda U2OS-39, contains an approximately 1.5 kb insert and was deposited with the ATCC on Jun. 16, 1987 under accession number 40345. The partial DNA sequence (compiled from lambda U20S-39 and several other hBMP-2A cDNA recombinants) and derived amino acid sequence are shown below in Table II. Lambda U20S-39 is expected to contain all of the nucleotide sequence necessary to encode the entire human counterpart of the protein BMP-2A encoded by the bovine gene segment whose partial sequence is presented in Table I. The BMP-2A protein encoded by Table II is contemplated to contain the 97 amino acid sequence from amino acid #299 to #396 or a sequence substantially homologous thereto. This human cDNA hBMP-2A contains an open reading frame of 1188 bp, encoding a protein of 396 amino acids. The protein is preceded by a 5' untranslated region of 342 bp with stop codons in all frames. The 13 bp region preceding this 5' untranslated region represents a linker used in the cDNA cloning procedure. This protein of 396 amino acids has a molecular weight of 45kd based on this amino acid sequence. It is contemplated that this sequence represents the primary translation product. It is further contemplated that BMP-2A may correspond to the approximately 18–20 kd subunit of Example IIC. The sequence corresponding to the sequence tryptic Fragment 3 of Example IV is underlined in Table II. The "pre" portion of the human BMP-2A protein is contemplated to comprise amino acid #1 to amino acid #23 as shown in Table II. The "pro" portion is contemplated to comprise amino acid #24 to amino acid #282 of Table II. The mature portion is contemplated to comprise amino acid #283 to #396 of Table II.

TABLE II

```
          10         20         30         40         50         60         70
GTCGACTCTA GAGTGTGTGT CAGCACTTGG CTGGGGACTT CTTGAACTTG CAGGGACAAT AACTTGCGCA 80         90        100        110        120        130        140
CCCCACTTTG CGCCGGTGCC TTTGCCCCAG CGGAGCCTGC TTCGCCATCT CCGAGCCCCA CCGCCCCTCC 150        160        170        180        190        200        210
ACTCCTCGGC CTTGCCCGAC ACTGAGACGCTGTTCCCAGC GTGAAAAGAG AGACTGCGCG GCCGGCACCC 220        230        240        250        260        270        280
GGGAGAAGGA GGAGGCAAAG AAAAGGAACG GACATTCGGT CCTTGCGCCA GGTCCTTTGA CCAGAGTTTT 290        300        310        320        330        340        350
TCCATGTGGA CGCTCTTTCA ATGGACGTGT CCCCGCGTGC TTCTTAGACG GACTGCGGTC TCCTAAAGGT (1)         370        385        400
CGACC ATG GTG GCC GGG ACC CGC TGT CTT CTA GCG TTG CTG CTT CCC CAG GTC
      MET Val Ala Gly Thr Arg Cys Leu Leu Ala Leu Leu Leu Pro Gln Val
```

TABLE II-continued

```
           415                 430                 445
CTC CTG GGC GGC GCG GCT GGC CTC GTT CCG GAG CTG GGC CGC AGG AAG TTC GCG
Leu Leu Gly Gly Ala Ala Gly Leu Val Pro Glu Leu Gly Arg Arg Lys Phe Ala 460                 475                 490                 505
GCG GCG TCG TCG GGC CGC CCC TCA TCC CAG CCC TCT GAC GAG GTC CTG AGC GAG
Ala Ala Ser Ser Gly Arg Pro Ser Ser Gln Pro Ser Asp Glu Val Leu Ser Glu 520                 535                 550                 565
TTC GAG TTG CGG CTG CTC AGC ATG TTC GGC CTG AAA CAG AGA CCC ACC CCC AGC
Phe Glu Leu Arg Leu Leu Ser MET Phe Gly Leu Lys Gln Arg Pro Thr Pro Ser 580                 595                 610
AGG GAC GCC GTG GTG CCC CCC TAC ATG CTA GAC CTG TAT CGC AGG CAC TCA GGT
Arg Asp Ala Val Val Pro Pro Tyr MET Leu Asp Leu Tyr Arg Arg His Ser Gly 625                 640                 655                 670
CAG CCG GGC TCA CCC GCC CCA GAC CAC CGG TTG GAG AGG GCA GCC AGC CGA GCC
Gln Pro Gly Ser Pro Ala Pro Asp His Arg Leu Glu Arg Ala Ala Ser Arg Ala 685                 700                 715
AAC ACT GTG CGC AGC TTC CAC CAT GAA GAA TCT TTG GAA GAA CTA CCA GAA ACG
Asn Thr Val Arg Ser Phe His His Glu Glu Ser Leu Glu Glu Leu Pro Glu Thr 730                 745                 760                 775
AGT GGG AAA ACA ACC CGG AGA TTC TTC TTT AAT TTA AGT TCT ATC CCC ACG GAG
Ser Gly Lys Thr Thr Arg Arg Phe Phe Phe Asn Leu Ser Ser Ile Pro Thr Glu 790                 805                 820                 835
GAG TTT ATC ACC TCA GCA GAG CTT CAG GTT TTC CGA GAA CAG ATG CAA GAT GCT
Glu Phe Ile Thr Ser Ala Glu Leu Gln Val Phe Arg Glu Gln MET Gln Asp Ala 850                 865                 880
TTA GGA AAC AAT AGC AGT TTC CAT CAC CGA ATT AAT ATT TAT GAA ATC ATA AAA
Leu Gly Asn Asn Ser Ser Phe His His Arg Ile Asn Ile Tyr Glu Ile Ile Lys 895                 910                 925                 940
CCT GCA ACA GCC AAC TCG AAA TTC CCC GTG ACC AGA CTT TTG GAC ACC AGG TTG
Pro Ala Thr Ala Asn Ser Lys Phe Pro Val Thr Arg Leu Leu Asp Thr Arg Leu 955                 970                 985
GTG AAT CAG AAT GCA AGC AGG TGG GAA AGT TTT GAT GTC ACC CCC GCT GTG ATG
Val Asn Gln Asn Ala Ser Arg Trp Glu Ser Phe Asp Val Thr Pro Ala Val MET 1000                1015                1030                1045
CGG TGG ACT GCA CAG GGA CAC GCC AAC CAT GGA TTC GTG GTG GAA GTG GCC CAC
Arg Trp Thr Ala Gln Gly His Ala Asn His Gly Phe Val Val Glu Val Ala His 1060                1075                1090                1105
TTG GAG GAG AAA CAA GGT GTC TCC AAG AGA CAT GTT AGG ATA AGC AGG TCT TTG
Leu Glu Glu Lys Gln Gly Val Ser Lys Arg His Val Arg Ile Ser Arg Ser Leu 1120                1135                1150
CAC CAA GAT GAA CAC AGC TGG TCA CAG ATA AGG CCA TTG CTA GTA ACT TTT GGC
His Gln Asp Glu His Ser Trp Ser Gln Ile Arg Pro Leu Leu Val Thr Phe Gly 1165                1180                1195                1210
CAT GAT GGA AAA GGG CAT CCT CTC CAC AAA AGA GAA AAA CGT CAA GCC AAA CAC
His Asp Gly Lys Gly His Pro Leu His Lys Arg Glu Lys Arg Gln Ala Lys His 1225                1240            (299)1255
AAA CAG CGG AAA CGC CTT AAG TCC AGC TGT AAG AGA CAC CCT TTG TAC GTG GAC
Lys Gln Arg Lys Arg Leu Lys Ser Ser Cys Lys Arg His Pro Leu Tyr Val Asp 1270                1285                1300                1315
TTC AGT GAC GTG GGG TGG AAT GAC TGG ATT GTG GCT CCC CCG GGG TAT CAC GCC
Phe Ser Asp Val Gly Trp Asn Asp Trp Ile Val Ala Pro Pro Gly Tyr His Ala 1330                1345                1360                1375
TTT TAC TGC CAC GGA GAA TGC CCT TTT CCT CTG GCT GAT CAT CTG AAC TCC ACT
Phe Tyr Cys His Gly Glu Cys Pro Phe Pro Leu Ala Asp His Leu Asn Ser Thr 1390                1405                1420
AAT CAT GCC ATT GTT CAG ACG TTG GTC AAC TCT GTT AAC TCT AAG ATT CCT AAG
Asn His Ala Ile Val Gln Thr Leu Val Asn Ser Val Asn Ser Lys Ile Pro Lys 1435                1450                1465                1480
GCA TGC TGT GTC CCG ACA GAA CTC AGT GCT ATC TCG ATG CTG TAC CTT GAC GAG
Ala Cys Cys Val Pro Thr Glu Leu Ser Ala Ile Ser MET Leu Tyr Leu Asp Glu
```

TABLE II-continued

```
         1495                1510                1525
AAT GAA AAG GTT GTA TTA AAG AAC TAT CAG GAC ATG GTT GTG GAG GGT TGT GGG
Asn Glu Lys Val Val Leu Lys Asn Tyr Gln Asp MET Val Val Glu Gly Cys Gly 1540 (396)     1553         1563        1573        1583        1593        1603
TGT CGC TAGTACAGCA AAATTAAATA CATAAATATA TATATATATA TATATTTTAG AAAAAAGAAA
Cys Arg

AAAA
```

Full-length BMP-2B human cDNA clones are obtained in the following manner. The 200 bp EcoRI-SacI fragment from the 5' end of the BMP-2B recombinant II-10-1 is isolated from its plasmid subclone, labeled by nick-translation, and hybridized to a set of duplicate nitrocellulose replicas of the U-2 OS cDNA library (25 filters/set; representing 500,000 recombinants). Hybridization and washing are performed under stringent conditions as described above. 16 duplicate positives are picked and replated for secondaries. Nitrocellulose filter replicas of the secondary plates are made and hybridized to an oligonucleotide which was synthesized to correspond to the sequence of II-10-1 and is of the following sequence:
CGGGCGCTCAGGATACTCAAGACCAGTGCTG
Hybridization is in standard hybridization buffer AT 50° C. with washing at 50° in 1 X SSC, 0.1% SDS. 14 recombinant bacteriophage which hybridize to this oligonucleotide are plaque purified. Plate stocks are made and small scale bacteriophage DNA preparations made. After suclalning 3 of these into M13, sequence analysis indicates that they represent clones which overlap the original BMP-2B clone.

One of these, lambda U2OS-3, was deposited with the ATCC under accession number 40342 on Jun. 16, 1987. U2OS-3 contains an insert of approximately 1.8 kb. The partial DNA sequence and derived amino acid sequence of U2OS-3 are shown below in Table III. This clone is expected to contain all of the nucleotide sequence necessary to encode the entire human BMP-2B protein. The BMP-2B protein encoded by Table III is contemplated to contain the 97 amino acid sequence from amino acid #311 to #408 or a sequence substantially homologous thereto. This cDNA contains an open reading frame of 1224 bp, encoding a protein of 408 amino acids, preceded by a 5' untranslated region of 394 bp with stop codons in all frames, and contains a 3' untranslated region of 308 bp following the in-frame stop condon. The 8 bp region preceding the 5' untranslated region represents a linker used in the cDNA cloning procedure. This protein of 408 amino acids has molecular weight of 47 kd and is contemplated to represent the primary translation product. A sequence similar though not idential to tryptic Fragment 3 of Example IV is underlined in Table III.

TABLE III

```
           10           20           30           40           50           60           70
       CTCTAGAGGG   CAGAGGAGGA   GGGAGGGAGG   GAAGGAGCGC   GGAGCCCGGC   CCGGAAGCTA   GGTGAGTGTG 80           90          100          110          120          130          104
       GCATCCGAGC   TGAGGGACGC   GAGCCTGAGA   CGCCGCTGCT   GCTCCGGCTG   AGTATCTAGC   TTGTCTCCCC 150          160          170          180          190          200          210
       GATGGGATTC   CCGTCCAAGC   TATCTCGAGC   CTGCAGCGCC   ACAGTCCCCG   GCCCTCGCCC   AGGTTCACTG 220          230          240          250          260          270          280
       CAACCGTTCA   GAGGTCCCCA   GGAGCTGCTG   CTGGCGAGCC   CGCTACTGCA   GGGACCTATG   GAGCCATTCC 290          300          310          320          330          340          350
       GTAGTGCCAT   CCCGAGCAAC   GCACTGCTGC   AGCTTCCCTG   AGCCTTTCCA   GCAAGTTTGT   TCAAGATTGG 360          370          380          390          400         (1)
       CTGTCAAGAA   TCATGGACTG   TTATTATATG   CCTTGTTTTC   TGTCAAGACA   CC  ATG ATT CCT
                                                                           MET Ile Pro 417                              432                        447                  462
       GGT AAC CGA ATG CTG ATG GTC GTT TTA TTA TGC CAA GTC CTG CTA GGA GGC GCG
       Gly Asn Arg MET Leu MET Val Val Leu Leu Cys Gln Val Leu Leu Gly Gly Ala 477                          492                       507
       AGC CAT GCT AGT TTG ATA CCT GAG ACG GGG AAG AAA AAA GTC GCC GAG ATT CAG
       Ser His Ala Ser Leu Ile Pro Glu Thr Gly Lys Lys Lys Val Ala Glu Ile Gln 522                      537                      552                    567
       GGC CAC GCG GGA GGA CGC CGC TCA GGG CAG AGC CAT GAG CTC CTG CGG GAC TTC
       Gly His Ala Gly Gly Arg Arg Ser Gly Gln Ser His Glu Leu Leu Arg Asp Phe 582                       597                   612                    627
       GAG GCG ACA CTT CTG CAG ATG TTT GGG CTG CGC CGC CGC CCG CAG CCT AGC AAG
       Glu Ala Thr Leu Leu Gln MET Phe Gly Leu Arg Arg Arg Pro Gln Pro Ser Lys 642                        657                     672
       AGT GCC GTC ATT CCG GAC TAC ATG CGG GAT CTT TAC CGG CTT CAG TCT GGG GAG
       Ser Ala Val Ile Pro Asp Tyr MET Arg Asp Leu Tyr Arg Leu Gln Ser Gly Glu
```

TABLE III-continued

|     | 687 |     |     |     |     | 702 |     |     |     |     | 717 |     |     |     |     | 732 |     |     |
|-----|-----|-----|-----|-----|-----|-----|-----|-----|-----|-----|-----|-----|-----|-----|-----|-----|-----|-----|
| GAG | GAG | GAA | GAG | CAG | ATC | CAC | AGC | ACT | GGT | CTT | GAG | TAT | CCT | GAG | CGC | CCG | GCC |
| Glu | Glu | Glu | Glu | Gln | Ile | His | Ser | Thr | Gly | Leu | Glu | Tyr | Pro | Glu | Arg | Pro | Ala |

|     |     | 747 |     |     |     |     | 762 |     |     |     |     | 777 |     |     |     |     |     |
|-----|-----|-----|-----|-----|-----|-----|-----|-----|-----|-----|-----|-----|-----|-----|-----|-----|-----|
| AGC | CGG | GCC | AAC | ACC | GTG | AGG | AGC | TTC | CAC | CAC | GAA | GAA | CAT | CTG | GAG | AAC | ATC |
| Ser | Arg | Ala | Asn | Thr | Val | Arg | Ser | Phe | His | His | Glu | Glu | His | Leu | Glu | Asn | Ile |

| 792 |     |     |     |     | 807 |     |     |     |     | 822 |     |     |     |     | 837 |     |     |
|-----|-----|-----|-----|-----|-----|-----|-----|-----|-----|-----|-----|-----|-----|-----|-----|-----|-----|
| CCA | GGG | ACC | AGT | GAA | AAC | TCT | GCT | TTT | CGT | TTC | CTC | TTT | AAC | CTC | AGC | AGC | ATC |
| Pro | Gly | Thr | Ser | Glu | Asn | Ser | Ala | Phe | Arg | Phe | Leu | Phe | Asn | Leu | Ser | Ser | Ile |

|     |     | 852 |     |     |     |     | 867 |     |     |     |     | 882 |     |     |     |     | 897 |
|-----|-----|-----|-----|-----|-----|-----|-----|-----|-----|-----|-----|-----|-----|-----|-----|-----|-----|
| CCT | GAG | AAC | GAG | GTG | ATC | TCC | TCT | GCA | GAG | CTT | CGG | CTC | TTC | CGG | GAG | CAG | GTG |
| Pro | Glu | Asn | Glu | Val | Ile | Ser | Ser | Ala | Glu | Leu | Arg | Leu | Phe | Arg | Glu | Gln | Val |

|     |     |     |     | 912 |     |     |     |     | 927 |     |     |     |     | 942 |     |     |     |
|-----|-----|-----|-----|-----|-----|-----|-----|-----|-----|-----|-----|-----|-----|-----|-----|-----|-----|
| GAC | CAG | GGC | CCT | GAT | TGG | GAA | AGG | GGC | TTC | CAC | CGT | ATA | AAC | ATT | TAT | GAG | GTT |
| Asp | Gln | Gly | Pro | Asp | Trp | Glu | Arg | Gly | Phe | His | Arg | Ile | Asn | Ile | Tyr | Glu | Val |

|     | 957 |     |     |     |     | 972 |     |     |     |     | 987 |     |     |     | 1002 |     |     |
|-----|-----|-----|-----|-----|-----|-----|-----|-----|-----|-----|-----|-----|-----|-----|------|-----|-----|
| ATG | AAG | CCC | CCA | GCA | GAA | GTG | GTG | CCT | GGG | CAC | CTC | ATC | ACA | CGA | CTA  | CTG | GAC |
| MET | Lys | Pro | Pro | Ala | Glu | Val | Val | Pro | Gly | His | Leu | Ile | Thr | Arg | Leu  | Leu | Asp |

|     |     |     | 1017 |     |     |     |     | 1032 |     |     |     |     | 1047 |     |     |     |     |
|-----|-----|-----|------|-----|-----|-----|-----|------|-----|-----|-----|-----|------|-----|-----|-----|-----|
| ACG | AGA | CTG | GTC  | CAC | CAC | AAT | GTG | ACA  | CGG | TGG | GAA | ACT | TTT  | GAT | GTG | AGC | CCT |
| Thr | Arg | Leu | Val  | His | His | Asn | Val | Thr  | Arg | Trp | Glu | Thr | Phe  | Asp | Val | Ser | Pro |

| 1062 |     |     |     |     | 1077 |     |     |     |     | 1092 |     |     |     |     | 1107 |     |     |
|------|-----|-----|-----|-----|------|-----|-----|-----|-----|------|-----|-----|-----|-----|------|-----|-----|
| GCG  | GTC | CTT | CGC | TGG | ACC  | CGG | GAG | AAG | CAG | CCA  | AAC | TAT | GGG | CTA | GCC  | ATT | GAG |
| Ala  | Val | Leu | Arg | Trp | Thr  | Arg | Glu | Lys | Gln | Pro  | Asn | Tyr | Gly | Leu | Ala  | Ile | Glu |

|     |     | 1122 |     |     |     |     | 1137 |     |     |     |     | 1152 |     |     |     |     | 1167 |
|-----|-----|------|-----|-----|-----|-----|------|-----|-----|-----|-----|------|-----|-----|-----|-----|------|
| GTG | ACT | CAC  | CTC | CAT | CAG | ACT | CGG  | ACC | CAC | CAG | GGC | CAG  | CAT | GTC | AGG | ATT | AGC  |
| Val | Thr | His  | Leu | His | Gln | Thr | Arg  | Thr | His | Gln | Gly | Gln  | His | Val | Arg | Ile | Ser  |

|     |     |     |     | 1182 |     |     |     |     | 1197 |     |     |     |     | 1212 |     |     |     |
|-----|-----|-----|-----|------|-----|-----|-----|-----|------|-----|-----|-----|-----|------|-----|-----|-----|
| CGA | TCG | TTA | CCT | CAA  | GGG | AGT | GGG | AAT | TGG  | GCC | CAG | CTC | CGG | CCC  | CTC | CTG | GTC |
| Arg | Ser | Leu | Pro | Gln  | Gly | Ser | Gly | Asn | Trp  | Ala | Gln | Leu | Arg | Pro  | Leu | Leu | Val |

|     | 1227 |     |     |     |     | 1242 |     |     |     |     | 1257 |     |     |     |     | 1272 |     |
|-----|------|-----|-----|-----|-----|------|-----|-----|-----|-----|------|-----|-----|-----|-----|------|-----|
| ACC | TTT  | GGC | CAT | GAT | GGC | CGG  | GGC | CAT | GCC | TTG | ACC  | CGA | CGC | CGG | AGG | GCC  | AAG |
| Thr | Phe  | Gly | His | Asp | Gly | Arg  | Gly | His | Ala | Leu | Thr  | Arg | Arg | Arg | Arg | Ala  | Lys |

|     |     | 1287 |     |     |     |     | 1302 |     |     |     |     | 1317 |     |     |     |     |     |
|-----|-----|------|-----|-----|-----|-----|------|-----|-----|-----|-----|------|-----|-----|-----|-----|-----|
| CGT | AGC | CCT  | AAG | CAT | CAC | TCA | CAG  | CGG | GCC | AGG | AAG | AAG  | AAT | AAG | AAC | TGC | CGG |
| Arg | Ser | Pro  | Lys | His | His | Ser | Gln  | Arg | Ala | Arg | Lys | Lys  | Asn | Lys | Asn | Cys | Arg |

| 1332(311) |     |     |     | 1347 |     |     |     |     | 1362 |     |     |     |     | 1377 |     |     |     |
|-----------|-----|-----|-----|------|-----|-----|-----|-----|------|-----|-----|-----|-----|------|-----|-----|-----|
| CGC       | CAC | TCG | CTC | TAT  | GTG | GAC | TTC | AGC | GAT  | GTG | GGC | TGG | AAT | GAC  | TGG | ATT | GTG |
| Arg       | His | Ser | Leu | Tyr  | Val | Asp | Phe | Ser | Asp  | Val | Gly | Trp | Asn | Asp  | Trp | Ile | Val |

|     | 1392 |     |     |     |     | 1407 |     |     |     |     | 1422 |     |     |     | 1437 |     |     |
|-----|------|-----|-----|-----|-----|------|-----|-----|-----|-----|------|-----|-----|-----|------|-----|-----|
| GCC | CCA  | CCA | GGC | TAC | CAG | GCC  | TTC | TAC | TGC | CAT | GGG  | GAC | TGC | CCC | TTT  | CCA | CTG |
| Ala | Pro  | Pro | Gly | Tyr | Gln | Ala  | Phe | Tyr | Cys | His | Gly  | Asp | Cys | Pro | Phe  | Pro | Leu |

|     |     |     | 1452 |     |     |     |     | 1467 |     |     |     |     | 1482 |     |     |     |     |
|-----|-----|-----|------|-----|-----|-----|-----|------|-----|-----|-----|-----|------|-----|-----|-----|-----|
| GCT | GAC | CAC | CTC  | AAC | TCA | ACC | AAC | CAT  | GCC | ATT | GTG | CAG | ACC  | CTG | GTC | AAT | TCT |
| Ala | Asp | His | Leu  | Asn | Ser | Thr | Asn | His  | Ala | Ile | Val | Gln | Thr  | Leu | Val | Asn | Ser |

|     | 1497 |     |     |     |     | 1512 |     |     |     |     | 1527 |     |     |     | 1542 |     |     |
|-----|------|-----|-----|-----|-----|------|-----|-----|-----|-----|------|-----|-----|-----|------|-----|-----|
| GTC | AAT  | TCC | AGT | ATC | CCC | AAA  | GCC | TGT | TGT | GTG | CCC  | ACT | GAA | CTG | AGT  | GCC | ATC |
| Val | Asn  | Ser | Ser | Ile | Pro | Lys  | Ala | Cys | Cys | Val | Pro  | Thr | Glu | Leu | Ser  | Ala | Ile |

|     |     | 1557 |     |     |     |     | 1572 |     |     |     |     | 1587 |     |     |     |     |     |
|-----|-----|------|-----|-----|-----|-----|------|-----|-----|-----|-----|------|-----|-----|-----|-----|-----|
| TCC | ATG | CTG  | TAC | CTG | GAT | GAG | TAT  | GAT | AAG | GTG | GTA | CTG  | AAA | AAT | TAT | CAG | GAG |
| Ser | MET | Leu  | Tyr | Leu | Asp | Glu | Tyr  | Asp | Lys | Val | Val | Leu  | Lys | Asn | Tyr | Gln | Glu |

| 1602 |     |     |     |     | 1617 |     |     | (408) |     | 1636 |     |      | 1646 |     | 1656 |
|------|-----|-----|-----|-----|------|-----|-----|-------|-----|------|-----|------|------|-----|------|
| ATG  | GTA | GTA | GAG | GGA | TGT  | GGG | TGC | CGC   | TGAGATCAGG | CAGTCCTTGA | GGATAGACAG |
| MET  | Val | Val | Glu | Gly | Cys  | Gly | Cys | Arg   |  |  |  |

|         | 1666       |         | 1676       |         | 1686       |         | 1696       |         | 1706       |         | 1716       | 1726       |
|---------|------------|---------|------------|---------|------------|---------|------------|---------|------------|---------|------------|------------|
| ATATACACAC | CACACACACA | CACCACATAC | ACCACACACA | CACGTTCCCA | TCCACTCACC | CACACACTAC |

|         | 1736       |         | 1746       |         | 1756       |         | 1766       |         | 1776       |         | 1786       | 1796       |
|---------|------------|---------|------------|---------|------------|---------|------------|---------|------------|---------|------------|------------|
| ACAGACTGCT | TCCTTATAGC | TGGACTTTTA | TTTAAAAAAA | AAAAAAAAAA | AATGGAAAAA | ATCCCTAAAC |

TABLE III-continued

| 1806 | 1816 | 1826 | 1836 | 1846 | 1856 | 1866 |
|---|---|---|---|---|---|---|
| ATTCACCTTG | ACCTTATTTA | TGACTTTACG | TGCAAATGTT | TTGACCATAT | TGATCATATA | TTTTGACAAA |
| 1876 | 1886 | 1896 | 1906 | 1916 | 1926 | 1936 |
| ATATATTTAT | AACTACGTAT | TAAAAGAAAA | AAATAAAATG | AGTCATTATT | TTAAAAAAAA | AAAAAAAACT |
| 1946 | | | | | | |
| CTAGAGTCGA | CGGAATTC | | | | | |

The sequences of BMP-2A and BMP-2B, as shown in Tables II and III, have significant homology to the beta (B) and beta (A) subunits of the inhibins. The inhibins are a family of hormones which are presently being investigated for use in contraception. See, A. J. Mason et al, Nature, 318:659–663 (1985). To a lesser extent they are also homologous to Mullerian inhibiting substance (MIS), a testicular glycoprotein that causes regression of the Mullerian duct during development of the male embryo, and transforming growth factor-beta (TGF-b) which can inhibit or stimulate growth of cells or cause them to differentiate. Furthermore, the sequences of Tables II and III indicate that BMP-2A and 2B have significant homology to the Drosophila decapentaplegic (DPP-C) locus transcript. See, J. Massague, Cell, 49:437–438 (1987); R. W. Padgett et al, Nature, 325:81–84 (1987); R. L. Cate et al, Cell 45: 685–698 (1986). It is considered possible therefore that a BMP-2 protein is the human homolog of the protein made from this transcript from this developmental mutant locus. BMP-2A and BMP-2B share sequence similarity with Vgl. Vgl mRNA has been localized to the vegetal hemisphere of Xenopus oocytes. During early development, it is distributed throughout the endoderm, but the mRNA is not detectable after blastula formation has occurred. The Vgl protein may be the signal used by the endorderm cells to commit ectodermal cells to become the embryonic mesoderm.

The procedures described above may be employed to isolate other related BMP-2 proteins of interest by utilizing the bovine BMP-2A and BMP-2B proteins as a probe source. Such other BMP-2 proteins may find similar utility in, inter alia, fracture repair, wound healing and tissue repair.

EXAMPLE VI

Expression of BMP-2A and BMP-2B

In order to produce bovine, human or other mammalian BMP-2 proteins, the DNA encoding it is transferred into an appropriate expression vector and introduced into mammalian cells or other preferred eukaryotic or prokaryotic hosts by conventional genetic engineering techniques. The presently preferred expression system for biologically active recombinant human BMP-2A and BMP-2B is stably transformed mammalian cells.

One skilled in the art can construct mammalian expression vectors by employing the sequence of Tables I-III or other modified sequences and known vectors, such as pCD [Okayama et al., Mol. Cell Biol., 2:161–170 (1982)] and pJL3, pJL4 [Gough et al., EMBO J., 4:645–653 (1985)]. The BMP-2 cDNA sequences can be modified by removing the non-coding nucleotides on the 5' and 3' ends of the coding region. The deleted non-coding nucleotides may or may not be replaced by other sequences known to be beneficial for expression. The transformation of these vectors into appropriate host cells can result in expression of BMP-2A or BMP-2B. One skilled in the art could manipulate the sequences of Tables I-III by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences there-from or altering nucleotides therein by other known techniques). The modified BMP-2A or BMP-2B coding sequence could then be inserted into a known bacterial vector using procedures such as described in T. Taniguchi et al., Proc. Natl Acad. Sci. USA, 77:5230–5233 (1980). This exemplary bacterial vector could then be transformed into bacterial host cells and a BMP-2 protein expressed thereby. For a strategy for producing extracellular expression of a BMP-2 protein in bacterial cells., see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a BMP-2 protein of the invention from mammalian cells involves the construction of cells containing multiple copies of the heterologous BMP-2 gene. The heterologous gene can be linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, J. Mol. Biol., 159:601–629 (1982). This approach can be employed with a number of different cell types. For example, a plasmid containing a DNA sequence for a BMP-2A or BMP-2B of the invention in operative association with other plasmid sequences enabling expression thereof and the DHFR expression plasmid pAdA26SV(A) 3 [Kaufman and Sharp, Mol. Cell. Biol., 2:1304 (1982)] can be co-introduced into DHFR-deficient CHO cells, DUKX-BII, by calcium phosphate coprecipitation and transfection, electroperation or protoplast fusion. DHFR expressing transformants are selected for growth in alpha media with dialyzed fetal calf serum, and subsequently selected for amplification by growth in increasing concentrations of MTX (sequential steps in 0.02, 0.2, 1.0 and 5uMMTX) as described in Kaufman et al., Mol Cell Biol., 5:1750 (1983). Transformants are cloned, and biologically active BMP-2A or BMP-2B expression is monitored by the Rosen-modified Sampath—Reddi rat bone formation assay described above in Example III. BMP-2A and BMP-2B expression should increase with increasing levels of MTX resistance. Similar procedures can be followed to produce other related BMP-2 proteins.

A. COS Cell Expression

As one specific example of producing a BMP-2 protein of Example V, the insert of II-3 (a λ GT10 derivative containing the full length BMP-2A cDNA) is released from the vector arms by digestion with EcoRI and subcloned into pSP65 yielding pBMP #39-3 or pSP65 BMP-2 #4. The insert is subcloned into the EcoRI site of the mammalian expression vector, pMT2CXM, or derivatives thereof. Plasmid DNA from this subclone is transfected into COS cells by the DEAE-dextran procedure [Sompayrac and Danna PNAS 78:7575–7578 (1981); Luthman and Magnusson, *Nucl. Acids Res.* 11: 1295–1308 (1983)] and the cells are cultured. Serum-free 24 hr. conditioned medium is collected from the cells starting 40–70 hr. post-transfection.

The mammalian expression vector pMT2 CXM is a derivative of p91023 (b) (Wong et al., *Science* 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, *Proc. Natl. Acad. Sci. USA* 82:689–693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in E. coli.

Plasmid pMT2 CXM is obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2CXM is then constructed using loopout/in mutagenesis (Morinaga,et al., Biotechnology 84: 636 (1984). This removes bases 1075 to 1145 relative to the starting from the Hind III site near the SV40 origin of replication and enhancer sequences of pMT2. In addition it inserts the following sequence:

5' PO_CATGGGCAGCTCGAG-3' at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

B. CHO Cell Expression

In order to achieve high levels of human BMP-2A protein, the DNA sequence of Table II encoding BMP-2A is inserted into a eucaryotic expression vector, stably introduced into CHO cells and amplified to high copy number by methotrexate selection of DHFR [R. J. Kaufman, et al., *EMBO J.* 6:189 (1987)].

A BMP-2A protein of Example V may be expressed in CHO cells by releasing the insert of pBMP #39-3 from the vector by digestion with EcoRI. The insert is subcloned into the EcoRI cloning site of the mammalian expression vector, pMT2CXM or derivative thereof. Alternatively, a derivative of BMP-2 in which the 5' untranslated region is deleted can be made by removal of the sequences contained between the SalI site at the 5' adapter (from the original cDNA cloning), and the SalI site 7 base pairs upstream of the initiator ATG, by digestion with SalI and religation. This step is conveniently performed in either SP65 derivatives containing the full length BMP-2A cDNA, but can also be performed in pMT2 derivatives. The 3' untranslated region can be removed using heteroduplex mutagenesis using the mutagenic oligonucleotide 5' GAGGGTTGTGGGTGTCGC<u>TAG</u>TGA <u>GTCGACT</u>ACAGCAAAATT Terminator SalI The sequence contains the terminal 3' coding region of the BMP-2A cDNA, followed immediately by a recognition site for SalI. The BMP-2A cDNA with deletions of the 5' and 3' untranslated regions can now be excised from pSP65 with SalI, and subcloned into the SalI site of pMT23. Plasmid DNA from the subclones are transfected into CHO cells by electroporation [Neuman et al, *EMBO J.*, 1:841–845 (1982)]. Two days later, cells are switched to selective medium containing 10% dialyzed fetal bovine serum and lacking nucleosides. Colonies expressing DHFR are counted 10–14 days later. Individual colonies or pools of colonies are expanded and analyzed for expression of BMP-2A RNA and protein using standard procedures and are subsequently selected for amplification by growth in increasing concentrations of MTX.

cDNA genes inserted into the EcoRI and/or Xho I sites will be expressed as a bicistronic mRNA with DHFR in the second position. In this configuration, translation of the upstream (BMP-2A) open reading frame is more efficient than the downstream (DHFR) cDNA gene [Kaufman et al, *EMBO J.* 6:187–193 (1987)]. The amount of DHFR protein expressed is nevertheless sufficient for selection of stable CHO cell lines.

Characterization of the BMP-2A polypeptides through pulse labeling with [35S] methionine or cystein and polyacrylamide gel electrophoresis indicates that multiple molecular size forms of BMP-2A proteins are being expressed and secreted from the stable CHO lines.

EXAMPLE VII

Biological Activity of Expressed BMP-2A and BMP-2B

To measure the biological activity of the expressed BMP-2A and BMP-2B proteins obtained in Example VI above, the proteins are recovered from the cell culture and purified. The purified protein is assayed in accordance with the rat bone formation assay described in Example III.

The COS expressed material of Example VI may be partially purified on a Heparin Sepharose column. 4 ml of the collected post transfection conditioned medium supernatant from one 100 mm culture dish is concentrated approximately 10 fold by ultrafiltration on a YM 10 membrane and then dialyzed against 20 mM Tris, 0.15 M NaCl, pH 7.4 (starting buffer). This material is then applied to a 1.1 ml Heparin Sepharose column in starting buffer. Unbound proteins are removed by an 8 ml wash of starting buffer, and bound proteins, including BMP-2 polypeptides, are desorbed by a 3–4 ml wash of 20 mM Tris, 2.0 M NaCl, pH 7.4.

The proteins bound by the Heparin column are concentrated approximately 10-fold on a Centricon 10 and the salt reduced by diafiltration with 0.1% trifluoroacetic acid. The appropriate amount of this solution is mixed with 20 mg of rat matrix and then assayed for in vivo bone and/or cartilage formation activity by the Rosen-modified Sampath—Reddi assay. A mock transfection supernatant fractionation is used as a control.

The implants containing rat matrix to which specific amounts of human BMP-2A or BMP-2B have been added are removed from rats after seven days and processed for histological evaluation. Representative sections from each implant are stained for the presence of new bone mineral with von Kossa and acid fuschin, and for the presence of cartilage-specific matrix formation using toluidine blue. The types of cells present within the section, as well as the extent to which these cells display phenotype are evaluated and scored as described in Example III.

Addition of the expressed human BMP-2A or BMP-2B to the matrix material resulted in formation of cartilage-like nodules at 7 days post implantation. The chondroblast-type cells were recognizable by shape and expression of metachromatic matrix. The amount of activity observed for human BMP-2A or BMP-2B indicates that it may be dependent upon the amount of human BMP-2A or BMP-2B protein added to the matrix sample.

Similar levels of activity are seen in the Heparin Sepharose fractionated COS cell extracts. Partial purification is accomplished in a similar manner as described above except that 6 M urea is included in all the buffers. A. Biological Activity and Characterization of BMP-2A Proteins To measure the biological activity of the BMP-2A proteins expressed in accordance with Example VIB above, 37 liters of the conditioned media is directly adsorbed to a 80 ml Heparin Sepharose column. The resin is washed with 0.15 M NaCl, 6.0 M urea, 20 mM Tris, pH 7.4 and then developed with a linear gradient to 1.0 M NaCl, 6.0 M urea, 50 mM Tris, pH 7.4. Fractions are assayed by the rat ectopic cartilage and bone formation assay described in Example III and the highest specific activity fractions pooled and concentrated by ultrafiltration on a YM-10 (Amicon) membrane. Protein concentration is determined by amino acid analysis.

The pooled material is analyzed by SDS-PAGE using a 12% acrylamide [U.K. Laemmli, Nature 227:680 (1970)] stained with silver [R. R. Oakley, et al. Anal. Biochem. 105:361 (1980)] and by immunoblot [H. Towbin, et al. Proc. Natl. Acad. Sci. USA 76:4350 (1979)] of 13.5% gel. SDS-PAGE reveals that multiple molecular size forms of BMP-2A proteins are being expressed and secreted from the stable CHO lines. Under non-reduced conditions, the major protein species is represented by a broad band at 30,000 daltons. Lower molecular weight species are seen as well as higher species, most notably 82,000 daltons and 113,000 daltons.

The 30,000 dalton band reacts with a rabbit antiserum directed against an E. coli produced fragment of BMP-2A amino acids #130–#396 as shown in Table II, with which it was incubated followed by 125I-Protein A. Under reduced conditions the 30,000 dalton material shifts to 16,000, 18,000, and 19,000 daltons. Each band is recognized by a turkey-derived anti-peptide antibody directed against amino acids #350–#365 as shown in Table II with which it is incubated coupled to bovine serum albumin with glutaraldehyde [J. P. Briand, et al. J. Immunol. Meth. 78:59 (1985)] in the presence of 100 ug/ml albumin followed by $^{125}$I-rabbit anti-turkey IgG, as well as the anti-BMP-2A antibody described above.

A major N-terminal amino acid sequence beginning at amino acid #283 as shown in Table II is obtained from the 30,000 dalton band isolated under non-reducing conditions.

The calculated subunit molecular weight of a protein of amino acids 283–396 is approximately 13,000 daltons. Preliminary experiments indicate that over 90% of the biological activity in the total protein pool is eluted from a non-reduced SDS-PAGE at a relative mass of 30,000 daltons. It is contemplated therefore that a dimer of amino acids #283–396 of BMP-2A, (referred to as a mature BMP-2A) accounts for the majority of the biological activity in the mixture of expressed BMP-2A proteins. It is further contemplated that processing of BMP-2A to the mature forms involves dimerization of the proprotein (amino acids #24 to #396) and removal of the N-terminal region in a manner analogous to the processing of the related protein TGF-b [L. E. Gentry, et al. Molec. & Cell Biol. 8:4162 (1988); R. Dernyck, et al. Nature 316:701 (1985)].

The broadness of the 30,000 dalton and the multiplicity 30 of its subunits are contemplated to arise from differences in carbohydrate in the potential N-glycosylation site or from aberrant proteolytic cleavage.

Immunoblot analysis of the 82,000 and 113,000 higher molecular weight species of BMP-2A under both non-reduced and reduced conditions suggests that these species may represent intermediate forms in the processing of the BMP-2A dimer. The 113 kd species is contemplated to comprise proprotein dimers of 113 kd (2 subunits of 66 kd) and the 83 kd species is contemplated to comprise a proprotein subunit linked to a mature BMP-2A subunit (66 kd plus 18 kd). Based on these analyses, approximately 50% of the total protein is active mature BMP-2A.

The pool of protein containing recombinant human BMP-2A is assayed in accordance with the rat cartilage and bone formation assay described in Example III using a modified scoring method as follows, three non-adjacent sections are evaluated from each implant and averaged. "+/–" indicates tentative identification of cartilage or bone; "+1" indicates 10% of each section being new cartilage or bone; "+2", >25%; "+3", >50%; "+4", –75%; "+5", >80%. A "–" indicates that the implant is not recovered. BMP-2A protein is implanted subcutaneously in rats for times ranging from 5–21 days and the resulting implants evaluated histologically for the presence of newly formed cartilage and bone. Additionally, the level of alkaline phosphatase, synthesized by both cartilage and bone cells is measured.

Addition of partially purified CHO expressed human BMP-2A to the matrix material induces both new cartilage and new bone formation. Implantation of amounts of 0.46–115.3 μg of BMP-2A tested for times ranging from 5–21 days results in the induction of new cartilage and bone formation. Induction of cartilage fromation is evident by day 7 and induction of bone formation is evident by day 14. The time at which bone formation occurs is related to the amount of BMP-2A implanted. At high doses bone can be observed at five days.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A composition comprising a purified protein produced by the steps of (a) culturing in a suitable culture medium a cell transformed with a DNA sequence comprising nucleotides #356 to #1543 as shown in FIG. 2; and (b) recovering and purifying the maulting secreted protein from said culture medium.

2. A composition comprising a purified protein produced by the steps of
   (a) culturing in a suitable culture medium a cell transformed with a DNA sequence comprising nucleotides #1 to #1543 as shown in FIG. 2; and
   (b) recovering and purifying from said culture medium a protein comprising amino acids #283–#396 of FIG. 2.

3. A composition comprising a purified protein produced by the steps of
   (a) culturine in a suitable culture medium a cell transformed with a DNA sequence comprising nucleotides #1202 to #1543 as shown in FIG. 2; and
   (b) recovering and purifying from said culture medium a protein comprising amino acids #283 to #396 of FIG. 2.

4. The composition of claim 3 wherein said transformed cell is mammalian.

5. The composition of claim 4 wherein said mammalian cell is CHO.

6. A composition comprising a purified protein produced by the steps of
   (a) culturine in a suitable culture medium a cell transformed with a DNA sequence comprising #356 to #1543 as shown in FIG. 2; and
   (b) recovering and purifying from said culture medium a protein comprising amino acids #283 to 396 of FIG. 2.

7. A composition comprising a purified protein characterized by amino acids #283 to #396 of FIG. 2.

8. The composition of claim 7 wherein said protein is a dimer.

9. The composition of claim 8 wherein each subunit is characterized by amino acid #283 to #396 of FIG. 2.

10. A composition of claim 9 further comprising a matrix for supporting said composition and providing a surface for bone and/or cartilage growth.

11. The composition of claim 10 wherein said matrix comprises a material selected from the group consisting of hydroxyapatite, collagen, polylactic acid and tricalcium phosphate.

12. A composition comprising a purified protein encoded by the DNA sequence of FIG. 2.

* * * * *